(12) United States Patent
Smith

(10) Patent No.: US 10,595,533 B1
(45) Date of Patent: Mar. 24, 2020

(54) BED BUG TREATMENT MIXTURE

(71) Applicant: Thomas Smith, Laurel, IN (US)

(72) Inventor: Thomas Smith, Laurel, IN (US)

(*) Notice: Subject to any disclaimer, the term of this patent is extended or adjusted under 35 U.S.C. 154(b) by 3 days.

(21) Appl. No.: 16/182,686

(22) Filed: Nov. 7, 2018

(51) Int. Cl.
*A01N 53/00* (2006.01)
*A01N 37/02* (2006.01)
*A01N 43/30* (2006.01)

(52) U.S. Cl.
CPC .............. *A01N 53/00* (2013.01); *A01N 37/02* (2013.01); *A01N 43/30* (2013.01)

(58) Field of Classification Search
CPC combination set(s) only.
See application file for complete search history.

(56) References Cited

U.S. PATENT DOCUMENTS

| 5,074,252 A | * | 12/1991 | Morgan, Jr. | ......... A01K 11/001 119/654 |
|---|---|---|---|---|
| 8,119,150 B2 | | 2/2012 | Tamarkin | |
| 9,247,751 B2 | | 2/2016 | Bessette | |
| 9,743,676 B2 | | 8/2017 | O'Connor | |
| 2008/0269177 A1 | | 10/2008 | Bessette | |
| 2009/0263511 A1 | | 10/2009 | Shah | |
| 2011/0135764 A1 | | 6/2011 | Enan | |
| 2016/0029625 A1 | | 2/2016 | Kennedy | |
| 2019/0389793 A1 | * | 12/2019 | Bedoukian | ............ C07C 69/708 |

FOREIGN PATENT DOCUMENTS

WO    WO2014149138    9/2014

OTHER PUBLICATIONS

Koganemaru, R. et al., "The bed bug problem: past, present, and future control methods," Pesticide Biochemistry and Physiology, vol. 106, pp. 177-189 (2013).*
HCAPLUS abstract 2015:376108 (2015).*
HCAPLUS abstract 2002:250009 (2002).*
King, W.V. Chemicals evaluated as insecticides and repellents at Orlando, FLA., Agriculture Handbook 69, U.S. Department of Agriculture, p. 182 (May 1954).*

* cited by examiner

*Primary Examiner* — John Pak

(57) ABSTRACT

A bed bug treatment mixture includes a liquid mixture that may be sprayed onto bedding having a bed bug, or *Cimex lectularius*, infestation so that the bed bugs and their eggs are killed by the mixture. The mixture includes a combination of permethrin, piperonyl butoxide, and glycolic acid as active ingredients and further includes one or more inactive ingredients.

7 Claims, No Drawings

BED BUG TREATMENT MIXTURE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to insecticide mixtures and more particularly pertains to a new insecticide mixture for killing bed bugs and the eggs thereof such that a bed bug infestation is eradicated and prevented from becoming an ongoing nuisance.

BRIEF SUMMARY OF THE INVENTION

An embodiment of the disclosure meets the needs presented above by generally comprising a liquid mixture that may be sprayed onto bedding having a bed bug, or *Cimex lectularius*, infestation so that the bed bugs and their eggs are killed by the mixture. The mixture includes a combination of permethrin, piperonyl butoxide, and glycolic acid as active ingredients and further includes one or more inactive ingredients.

There has thus been outlined, rather broadly, the more important features of the disclosure in order that the detailed description thereof that follows may be better understood, and in order that the present contribution to the art may be better appreciated.

There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

Not Applicable

DETAILED DESCRIPTION OF THE INVENTION

A new insecticide mixture embodying the principles and concepts of an embodiment of the disclosure will now be described.

As best stated herein, the bed bug treatment mixture 10 generally comprises a mixture that is sprayed onto bedding, such as mattresses and box springs in particular, to kill and prevent the spread of *Cimex lectularius*, commonly referred to as bed bugs.

The mixture includes what is commonly known as permethrin, also known as (±)-3-Phenoxybenzyl 3-(2,2-dichlorovinyl)-2,2-dimethylcyclopropanecarboxylate. (1R,3S)-trans and (1R,3R)-cis enantiomers are two of the four eantiomers used for insecticide wherein the cis component is between 35% and 35% of the permethrin. Permethrin has a chemical composition typically of $C_{21}H_{20}Cl_2O_3$. The mixture contains between 0.005% and 0.006% of permethrin and may specifically comprise 0.00547% of permethrin.

The mixture further includes piperonyl butoxide, $C_{19}H_{30}O_5$, which is further known as 5-[2-(2-butoxyethoxy)ethoxymethyl]-6-propyl-1,3-benzodioxole. The piperonyl butoxide comprises between 0.02% and 0.03% of the mixture and specifically may comprise 0.02735% of the mixture.

A third ingredient of the active ingredients is glycolic acid, $C_2H_4O_3$, which is also known as 2-Hydroxyethanoic acid. The glycoloic acid makes up between 0.1% and 0.2% of the mixture and may specifically make up 0.16415% of the mixture.

Active ingredients may be added to the mixture and will generally comprise water wherein the mixture will comprise at least 80% water and may comprise more than 85% water.

In use, the mixture is sprayed onto mattresses, box springs and areas where bed bugs reside and lay eggs. The mixture kills the bed bugs as well as the eggs to prevent the eggs from hatching and prolonging the infestation. While highly effective against the bed bugs, the mixture is safe to use around humans and pets.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An insecticide mixture configured to kill and eliminate *Cimex lectularius*, said mixture comprising:
   permethrin;
   piperonyl butoxide;
   glycolic acid; and
   inactive ingredients.

2. The insecticide mixture configured to kill and eliminate *Cimex lectularius* according to claim 1, wherein said perimethrin comprising (1R,3S)-trans and (1R,3R)-cis enantiomers of (±)-3-Phenoxybenzyl 3-(2,2-dichlorovinyl)-2,2-dimethylcyclopropanecarboxylate, wherein said (1R,3R)-cis comprises at least 35% and no more than 65% of said permethrin.

3. The insecticide mixture configured to kill and eliminate *Cimex lectularius* according to claim 1, wherein said permethrin comprises between 0.005% and 0.006% of said mixture.

4. The insecticide mixture configured to kill and eliminate *Cimex lectularius* according to claim 3, wherein said piperonyl butoxide comprises between 0.02% and 0.03% of said mixture.

5. The insecticide mixture configured to kill and eliminate *Cimex lectularius* according to claim 4, wherein said glycolic acid comprising between 0.1% and 0.2% of said mixture.

6. The insecticide mixture configured to kill and eliminate *Cimex lectularius* according to claim 1, wherein said inactive ingredients includes water, said water comprising at least 80% of said mixture.

7. An insecticide mixture configured to kill and eliminate *Cimex lectularius*, said mixture comprising:
   permethrin, said perimethrin comprising (1R,3S)-trans and (1R,3R)-cis enantiomers of (±)-3-Phenoxybenzyl 3-(2,2-dichlorovinyl)-2,2-dimethylcyclopropanecarboxylate, wherein said (1R,3R)-cis comprises at least 35% and no more than 65% of said permethrin;
   piperonyl butoxide;
   glycolic acid;
   inactive ingredients;
   said permethrin comprising between 0.005% and 0.006% of said mixture;
   said piperonyl butoxide comprising between 0.02% and 0.03% of said mixture;
   said glycolic acid comprising between 0.1% and 0.2% of said mixture;
   said inactive ingredients including water, said water comprising at least 80% of said mixture.

* * * * *